(12) United States Patent
Stephens et al.

(10) Patent No.: US 6,783,541 B2
(45) Date of Patent: Aug. 31, 2004

(54) METHODS FOR INHIBITING OR SUPPRESSING STENOSIS OF ARTERIOVENOUS ACCESS FISTULAS AND GRAFTS

(75) Inventors: W. Patrick Stephens, Santa Rosa, CA (US); Steven John Rychnovsky, Santa Barbara, CA (US); Jeffrey P. Walker, Goleta, CA (US); Heidi Nielsen, Lyngby (DK); Christina Ann Waters, Leucadia, CA (US); John S. Hill, Solvang, CA (US)

(73) Assignee: Miravant Medical Technologies, Inc., Santa Barbara, CA (US)

( * ) Notice: Subject to any disclaimer, the term of this patent is extended or adjusted under 35 U.S.C. 154(b) by 0 days.

(21) Appl. No.: 09/991,275

(22) Filed: Nov. 21, 2001

(65) Prior Publication Data

US 2003/0100934 A1 May 29, 2003

(51) Int. Cl.[7] .................................................. A61B 6/00
(52) U.S. Cl. ............................. 607/88; 607/89; 607/92; 606/7; 606/8; 606/15; 128/898
(58) Field of Search ............................ 606/7, 108, 128; 607/88, 89; 623/1.1, 1.23; 604/19–21, 27–30; 128/898; 600/310

(56) References Cited

U.S. PATENT DOCUMENTS

| | | | |
|---|---|---|---|
| 5,370,608 A | * 12/1994 | Sahota et al. ................. 604/20 |
| 5,419,760 A | 5/1995 | Narciso, Jr. ..................... 604/8 |
| 5,422,362 A | 6/1995 | Vincent et al. |
| 5,674,192 A | * 10/1997 | Sahatjian et al. .............. 604/28 |
| 5,773,609 A | 6/1998 | Robinson et al. |
| 5,786,326 A | 7/1998 | Horwitz |
| 5,824,080 A | * 10/1998 | Lamuraglia ................... 623/11 |
| 5,972,928 A | 10/1999 | Chatterjee .................... 514/212 |
| 6,008,211 A | 12/1999 | Robinson et al. |
| 6,026,316 A | 2/2000 | Kucharczyk et al. ....... 600/420 |
| 6,054,449 A | 4/2000 | Robinson et al. |
| 6,210,393 B1 | 4/2001 | Brisken |
| 6,387,116 B1 | * 5/2002 | McKenzie et al. ............ 623/1.1 |
| 6,468,244 B1 | 10/2002 | Leone et al. ........... 604/103.02 |
| 6,609,014 B1 | * 8/2003 | Allison et al. .............. 600/310 |

FOREIGN PATENT DOCUMENTS

| | | | | |
|---|---|---|---|---|
| WO | WO 01/00106 A1 | 1/2001 | | |
| WO | WO 01/35996 A2 | 5/2001 | | |
| WO | 01/35996 A2 | * 5/2001 | .......... A61K/41/00 |
| WO | WO 01/35997 A2 | 5/2001 | | |

OTHER PUBLICATIONS

Dr. N. R. ChandraSekar "Photodynamic Therapy– A Tool for Treating Vascular Restenosis." http://mgh.harvard.edu/news/Winter1994/PDTool.html.*

Ortu, P. et al. "Photodynamic Therapy of Arteries: A Novel Approach for Treatment of Experimental Intimal Hyperplasia," *Circulation* Mar. 1992, 85(3): 1189–1196.

LaMuraglia, G.M., "Choloraluminum Sulfonated Phthalocyanine Partioning in Normal and Intimal Hyperplastic Artery in the Rat: Implications for Photodynamic Therapy," *American Journal of Pathology* Jun. 1993, 142(6): 1898–1905.

(List continued on next page.)

Primary Examiner—Linda C. M. Dvorak
Assistant Examiner—Ahmed Farah
(74) Attorney, Agent, or Firm—Bryan Cave LLP

(57) ABSTRACT

A method for inhibiting or suppressing stenosis associated with an arteriovenous access. A dosage of photosensitive compound is introduced into the artery or vein. An anastomotic area of the artery or vein is then exposed to a source of light having a wavelength suitable for photoactivating the photosensitive compound for a period of time sufficient to provide a therapeutic effect. A method is also described for the delivery of drugs into the anastomotic site of an AV access to inhibit the formation of stenotic lesions at those sites.

18 Claims, 2 Drawing Sheets

OTHER PUBLICATIONS

LaMuraglia, G.M., et al., "Photodynamic Therapy Inhibition of Experimental Intimal Hyperplasia: Acute and Chronic Effects," *Journal of Vascular Surgery* Feb. 1994, 19(2): 321–331.

Grant, W.E., et al., "Photodynamic Therapy of Normal Rat Arteries After Photosensitisation Using Disulphonated Aluminum Phthalocyanine and 5–aminolaevulinic Acid," 1994.

ChandraSekar, N.R., "Photodynamic Therapy—A Tool for Treating Vascular Restonosis," http://mghlc.mgh.harvard.edu/news/Winter1994/PDTool.html.

Sobeh, M.S., et al., "Photodynamic Therapy in a Cell Culture Model of Human Intimal Hyperplasia," Eur J. Vasc. Endovasc. Surg. May 1995, 9(4): 463–8. (Abstract).

LaMuraglia, G. M., et al., "Photodynamic Therapy of Vein Grafts: Suppression of Intimal hyperplasia of the vein graft but not the anastomosis," J. Vasc. Surg. Jun. 1995, 21: 882–390.

LaMuraglia, G.M., et al., "Photodynamic Therapy Inhibits Experimental Allograft Rejection: A Novel Approach for Development of Vascular Bioprosthesis," *Circulation* Oct. 1, 1995, 92(7): 1919–1926.

Overhaus, M., et al., "Photodynamic Therapy Generates a Matrix Barrier to Invasive Vascular Cell Migration," *Circulation* Research Feb. 18, 2000, 334–340.

Yamagnchi, A., Reduction of Vein Graft Disease Using Photodynamic Therapy with Motexafin Lutetium in a Rodent Isograft Model, *Circulation* Nov. 7, 2000, III–275–III–280.

Walker, J., et al., "The Photopoint™ Catheter Based System for the Treatment of Intimal Hyperplasia," Cardiovascular Radiation Therapy V & Restenosis Forum, Washington, D.C., Feb. 7, 2001.

LaMuraglia, G.M., et al., "Photodynamic Therapy Induces Apoptosis in Intimal Hyperplastic Arteries," Am. J. Pathol. 2000 Sep; 157(3): 867–875. (Abstract).

* cited by examiner

METHODS FOR INHIBITING OR SUPPRESSING STENOSIS OF ARTERIOVENOUS ACCESS FISTULAS AND GRAFTS

FIELD OF THE INVENTION

The present invention relates to methods for using photodynamic therapy (PDT) to inhibit or suppress stenoses of arteriovenous (AV) access fistulas and grafts.

BACKGROUND

Patients suffering from chronic renal failure must typically receive dialysis treatment two to three times a week. The most widely used form of dialysis is hemodialysis. In hemodialysis, blood is pumped out of the patient's body to an artificial kidney machine that removes waste and excess fluid from the blood. Treated blood is returned to the patient's body.

Figure 1:
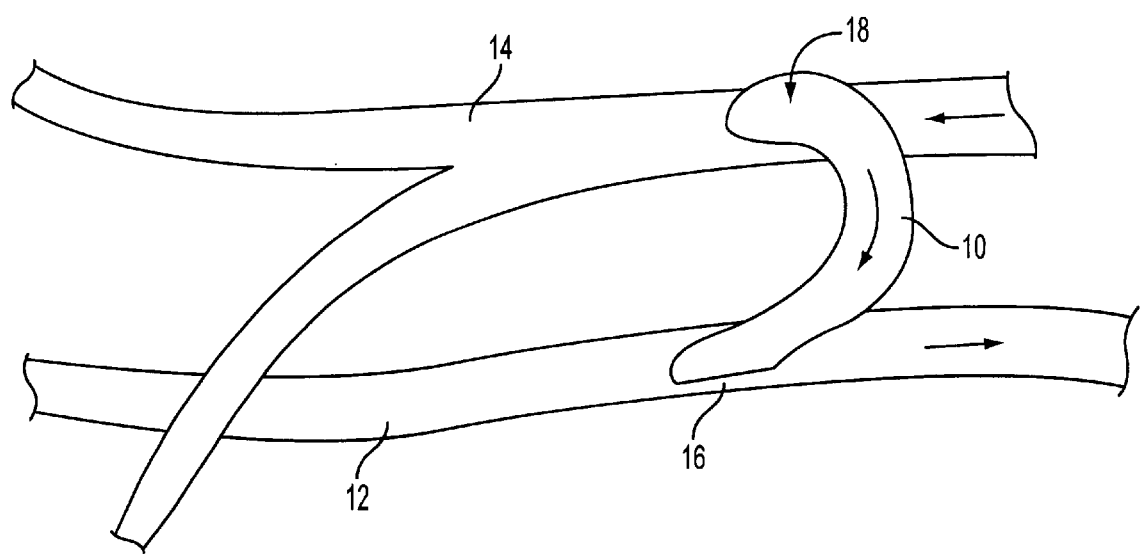

An AV access is a subcutaneous access placed by minor surgery typically in the forearm to provide a site to connect hemodialysis needles. An AV access graft is a commonly used type of AV access for hemodialysis. FIG. 1 illustrates a typical AV access graft, which is created by attaching a graft 10 between a vein 12 and an artery 14.

A significant problem associated with AV access for long-term dialysis patients is frequent AV access failure. Primary patency rates for AV access are extremely low. [Hodges, C. H. et al, Longitudinal comparison of dialysis access methods: Risk factors for failure. *J Vasc. Surgery* December 1997] (reporting 1-year primary patency rates for AV access fistulas and polytetraflouroethylene (PTFE) AV access grafts at 43% and 41% respectively). A frequent cause of permanent peripheral hemodialysis AV access failure is vascular stenosis, which occurs most frequently at the venous anastomotic site. This stenosis is generally believed to be the result of a persistent injury condition that occurs at the venous anastomotic site as a result of the pressure differential that exists between the arterial and venous systems and the associated disruption in the local rheodynamics.

Traditionally, surgical procedures such as thrombectomy and balloon angioplasty have been used to treat stenosis of AV access sites. However, such traditional treatment methods have had dismal results. Although an access may be restored with traditional intervention, such as percutaneous translumenal angioplasty (PTA), repeated failure is likely due to the persistent nature of the injury condition. As a result, efforts to utilize balloon angioplasty to prophylactically prolong the patency of AV accesses have not demonstrated a significant prolongation of graft and fistula patency. Thus, there is a significant need for an improved method for effectively preventing or removing stenotic lesions associated with AV access, particularly those located in the vicinity of the venous anastomotic site.

PDT is a relatively new method that is under development for the treatment of various diseases including cancer, psoriasis, arterial plaques and restenosis, macular degeneration, glaucoma, and certain viral infections. The PDT procedure is conducted by administering a photosensitizer drug to the desired treatment zone, by either local or systemic means, followed by exposure to photoactivating light. The photoactivating light excites the photosensitizer, which in turn generates toxic species such as singlet oxygen, oxygen radicals, peroxide radicals or other radical species which generate a PDT effect, as is well known to those skilled in the art. These toxic species interact with tissues in which the photosensitizer is localized, resulting in modification or destruction of the tissue and the desired clinical effect.

In the case of arterial plaques and restenosis, PDT has been demonstrated in numerous animal models and has recently been introduced in a clinical study. One example of early work in this field is that done by Ortu et al. [Photodynamic Therapy of Arteries: A Novel Approach for Treatment of Experimental Intimal Hyperplasia, *Circulation*, 85: 1189–1196, March 1992]. In that study the injury usually associated with arterial restenosis was simulated and then treated with PDT in an effort to inhibit the development of intimal hyperplasia. During the past decade numerous other studies have been conducted in an effort to either inhibit the development of intimal hyperplasia in arteries or to reduce the plaque that has developed within an artery.

In contrast to the arterial system, only limited studies report the use of PDT for treatment of stenotic lesions within the venous system. Part of the reason for this is likely due to the very different biology associated with veins and arteries. Although both veins and arteries serve as blood conduits, their structure and biological response mechanisms are significantly different. For example, in the case of AV access, the stenoses occurring in the anastomotic region has been hypothesized to arise, at least in part, from the pressure differential between the arterial and venous systems, as well as from turbulence that exists near the anastomotic sites. Such conditions do not exist in the standard arterial injuries for which PDT has previously been investigated. Similarly, they do not exist in the case of interpositional grafts such as those studied by LaMuraglia and described below. Given the different nature of the injury responsible for the stenosis in AV access as well as the lack, to date, of a safe and effective means of treating such stenoses, it has not been demonstrated whether a treatment used to treat intimal hyperplasia in arteries will inhibit or suppress stenotic lesions at the anastomosis in AV access sites.

LaMuraglia et al. [Photodynamic Therapy of Vein Grafts: Suppression of Intimal Hyperplasia of the Vein Graft but not the Anastomosis, *J of Vascular Surgery*, Vol. 21, No 6: June 1995] reports the use of PDT for the suppression of intimal hyperplasia in autologous vein grafts. In that work an autologous bypass graft in a rat model was treated with PDT in an effort to inhibit intimal hyperplasia. The rats were first given a systemic injection of a photosensitizer drug and at 24 hours after drug injection a section of the jugular vein was surgically removed. Following removal, the harvested vein section received light treatment (ex-vivo) to induce the PDT effect. This vein section was then used as an interpositional graft of the carotid artery of the animal from which it had been harvested. This was done by first removing a short section of carotid artery, then suturing the section of treated vein into its place, oriented properly for blood flow. Results of this study did not provide any measurable inhibition of the intimal hyperplasia occurring at the anastomosis at either end of the interpositional graft.

The results noted in LaMuraglia et al. suggest that their treatment method would not be an effective treatment for AV access sites, since the most common location of stenosis is at the venous anastomosis site [Chapter 74: Arteriovenous Grafts in Vascular Diseases: Surgical and Interventional Therapy, Churchill Livingstone Publishers, January 1994, pg. 1055–1062, ISBN: 0443088411]. Specifically, LaMuraglia's approach, consisting of ex-vivo treatment of the graft but not the anastomosis, failed to demonstrate a viable graft as a result of the formation of stenosis at the anastomosis site.

Based on the lack of success with previous approaches, there exists a strong need for an effective method of treating stenoses in AV access fistulas and grafts. While PDT has been shown to be a promising treatment for inhibiting or suppressing stenosis associated with intimal hyperplasia in arteries, similar results have not been demonstrated in the treatment of stenosis in AV access fistulas and grafts. Furthermore no method has been demonstrated to effectively reduce stenosis of AV access fistulas or grafts while safely preserving the viability of the vessel at the site of the anastomosis.

SUMMARY

The present invention relates to a method for safely and effectively inhibiting or suppressing stenosis associated with an arteriovenous access connecting an artery and a vein, each having an anastomotic area. At least one of the blood vessels is contacted with a photosensitive compound (e.g., by local or systemic administration). Target tissue which includes the anastomotic area of the contacted blood vessel is exposed to a source of light having a wavelength suitable for photoactivating the photosensitive compound for a period of time sufficient to provide a therapeutic effect.

In the case of inhibiting stenosis formation, the anastomotic area can be exposed to the source of light either before or after graft implantation or creation of the fistula. For existing lesions, the light can also be delivered transcutaneously if the drug is delivered locally. In one embodiment, the photosensitizer drug is endolumenally incubated in the blood vessel for a sufficient time to allow the compound to diffuse into the blood vessel. In a second embodiment, the photosensitzer drug is administered into the isolated portion of the blood vessel using transcutaneous access via the graft, adjacent artery or adjacent vein. In a third embodiment, the photosensitizer drug is administered systemically via intravenous delivery. In a fourth embodiment, the photosensitizer drug is delivered directly to the target site using a local drug delivery device.

Alternatively, a sleeve or cuff may be placed around the surgically exposed blood vessel for incubating the photosensitive compound within the sleeve or cuff so that the photosensitizer drug is kept in contact with a wall of the blood vessel for a sufficient time to allow the compound to diffuse into the vessel wall.

The dosage of photosensitive compound may also be administered by applying a semisolid substance (e.g., a gel-like substance or paste) containing the photosensitizer drug directly to the wall of the blood vessel.

Light treatment can be delivered to the anastomotic area of the blood vessel using either an intralumenal light delivery catheter or using an external light delivery device.

A shield can be placed between the irradiation site encompassing the vessel anastomosis and the surrounding tissue during light exposure to prevent excitation of any drug in surrounding tissue. Alternatively, a cuff or sleeve that limits light transmission can be implanted around the graft or anastomotic area of the blood vessel at the time of graft implantation to allow later intralumenal light treatment using a deeply penetrating wavelength of light without exposing the tissue surrounding the graft.

DRAWINGS

Figure 2A:
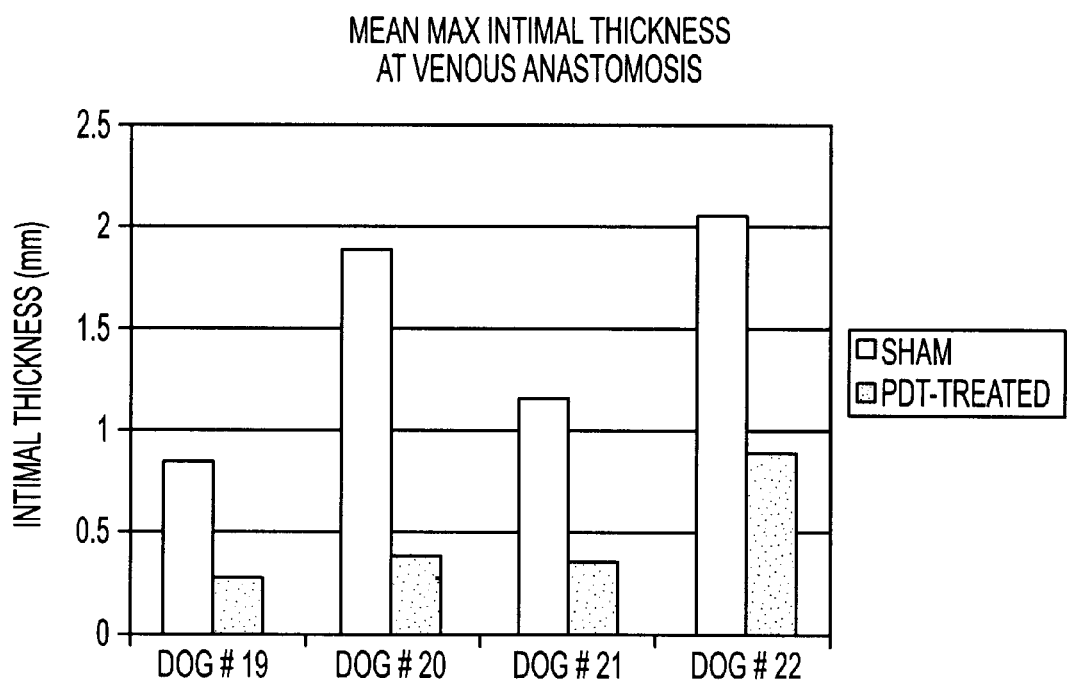
Figure 2B:
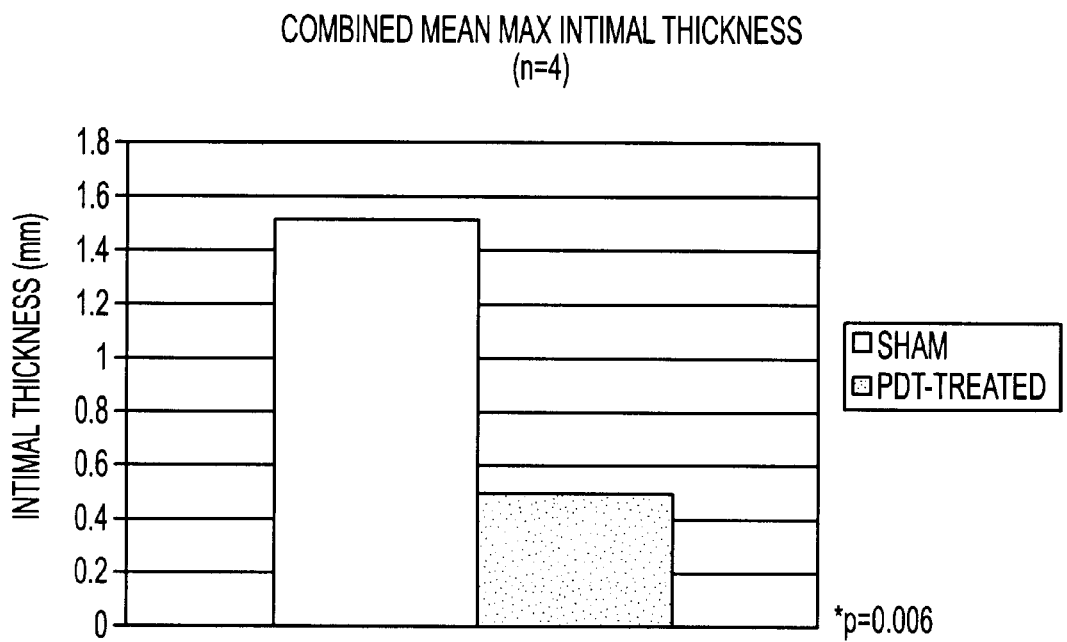

FIG. 1 is a perspective view of a typical AV access graft;
FIG. 2A is a bar chart showing thickness of experimental stenotic lesions at the venous anastomosis four weeks after treatment of AV graft anastomosis in a canine model; and FIG. 2B is a bar chart of combined mean thickness of the experimental stenotic lesions at the venous anastomosis four weeks after treatment of AV graft anastomosis in a canine model.

The drawings are provided for illustrative purposes only and should not be used to unduly limit the scope of the invention.

DETAILED DESCRIPTION

The present invention relates to the use of PDT for inhibiting or suppressing stenosis associated with AV access fistulas and grafts to prolong the life of the AV access.

AV access refers generally to any type of subcutaneous access comprising a connection between an artery and a vein, including (without limitation) AV access fistulas and AV access grafts. An AV access is typically placed by minor surgery in a limb, such as a forearm, to provide a site to connect hemodialysis needles. An AV access may be created in a number of ways. For example, an internal AV fistula (a surgical or pathological connection between an artery and a vein) may be surgically created by connecting a vein and an artery that lie parallel to each other. The increased pressure in the vein causes the vein to swell and the walls of the vein to strengthen, forming a large superficial vessel that is accessible to venipuncture. Another way of creating an AV access is by tying a vein off distally and attaching it directly to an artery. Another form of AV access is an AV access graft, which is a synthetic or tissue graft connecting an artery and a vein. Synthetic AV access grafts are typically made from polytetraflouroethylene (PTFE). AV access grafts can also be made from a heterologous or autologous blood vessel graft.

FIG. 1 illustrates a typical AV access graft. A graft 10 is connected at one end to a vein 12 at anastomotic area 16 of the vein 12. The graft 10 is connected to the artery 14 at its other end at the anastomotic area 18 of the artery. An AV access graft is usually anastomosed to the blood vessels in an end to side fashion. As used herein the term anastomotic area refers generally to the portion of the artery or vein to which the graft or blood vessel is or will be connected. That term is used to refer to any such area either before or after actual connection of the graft or formation of the fistula. The anastomotic areas are the areas where stenosis primarily develops.

The methods described herein may be employed either to inhibit stenosis formation or to suppress an existing stenosis. The PDT treatment parameters preferably are such that significant acellularity is induced in the anastomotic area being treated. Lower doses, while potentially having limited benefit, may not provide the efficacy that is desired of an effective treatment scheme. Furthermore, use of PDT doses sufficient to induce significant acellularity have not been found to result in adverse clinical symptoms. Therefore, this method provides both a safe and effective treatment of stenosis occurring at the anastomotic area in AV access sites.

For inhibiting stenosis, the PDT is preferably used to prophylactically treat AV access fistulas and grafts to prolong their primary or secondary patency relative to the non-PDT treated case. Inhibition of stenosis is preferably achieved by inducing at least partial acellularity within the vessel wall at the anastomotic area. As a result of this depletion in cell population, the amount of cellular proliferation is reduced, thereby minimizing, or at least slowing, the development of stenotic lesions. This inhibition can be further enhanced over the long term by the development of an endothelial cell layer lining the vessel lumen within the anastomotic area following PDT treatment.

In the case of suppression of an existing stenosis, PDT preferably follows a recanalization procedure (typically thrombectomy or balloon angioplasty). However, when treating a lumen with only partial stenosis, PDT treatment can be used to directly treat the stenosis in order to stabilize it, without any additional recanalization procedure. The purpose of the PDT treatment in this case is to suppress cell growth and stabilize the lesion through, for example, collagen cross-linking, and to provide a prolonged patency relative to the non-PDT treated approach. Suppression of stenosis is achieved by inducing at least partial acellularity within the vessel wall and/or stenotic lesion. For the case of stenosis located within the AV access, the target tissue for this cell depletion is the tissue of the stenotic lesion. For the case of stenosis located within the vessel but in the region of the anastomotic area, the primary target tissue of the treatment is the stenotic lesion with the secondary target tissue being the underlying tissue of the vessel wall. In either case, reduction in this cell population leads to an overall reduction in the cross sectional area of the stenosis and further stabilizes the lesion. Furthermore, depletion of this cell population inhibits further development of the stenotic lesion, similar to the case of inhibition described earlier. Long term suppression is enhanced by the development of an endothelial cell layer within the anastomotic area following PDT treatment.

The treatment methods described herein can be done at the time of the surgical placement of the access or may be employed in conjunction with a diagnostic technique designed to detect the amount of stenosis. Examples of diagnostic techniques to be used include ultrasound and measurement of pressure differentials.

The methods of the present invention include the step of contacting the target blood vessel with a dosage of photosensitive compound. The photosensitizer drug used may be from any one of a variety of known compounds such as those listed in Table 1.

TABLE 1

Classes of Photosensitive Compounds

Pyrrole-derived macrocyclic compounds
Naturally occurring or synthetic porphyrins and derivatives thereof
Naturally occurring or synthetic chlorins and derivatives thereof
Naturally occurring or synthetic bacteriochlorins and derivatives thereof
Synthetic isobacteriochlorins and derivatives thereof
Phthalocyanines and derivatives thereof
Naphthalocyanines and derivatives thereof
Porphycenes and derivatives thereof
Porphycyanines and derivatives thereof
Pentaphyrin and derivatives thereof
Sapphyrins and derivatives thereof
Texaphyrins and derivatives thereof
Phenoxazine dyes and derivatives thereof
Phenothiazines and derivatives thereof
Chalcoorganapyrylium dyes and derivatives thereof
Triarylmethanes and derivatives thereof
Rhodamines and derivatives thereof
Fluorescenes and derivatives thereof
Azaporphyrins and derivatives thereof
Benzochlorins and derivatives thereof
Purpurins and derivatives thereof
Chlorophylls and derivatives thereof
Verdins and derivatives thereof
Psoralens and derivatives thereof The above list is provided by way of example only and is not intended to be exhaustive. Those skilled in the art will appreciate that other compounds can be used with the methods of the present invention to provide the desired therapeutic effect.

Certain classes of photosensitive compounds are particularly suited for the treatment of stenosis associated with intimal hyperplasia because they have been shown to localize in vascular smooth muscle cells. However, when light shielding is used, the methods described herein are not specific to a particular type of photosensitizer or mechanism of localization. Rather this technique can be used for any photosensitizer drug that is taken up within the target vessel to a sufficient degree to allow a sufficient PDT effect using reasonable light doses. Alternatively, when transcutaneous light delivery without shielding is used, a photosensitizer with high selectivity for the vessel wall or one that can be selectively delivered directly to the vessel wall using a local delivery means is preferred.

The photosensitive drug can be delivered either locally or systemically in the appropriate dosage. The photosensitive drug can be delivered locally by any one of a variety of methods such as, for example, those described below. Preferably, the blood vessel to be treated is temporarily occluded and flushed with a liquid that is transparent at the treatment wavelength in order to allow more uniform excitation of the drug.

The photosensitive drug can be intravenously delivered to the blood vessel and incubated endolumenally for sufficient periods of time to allow drug uptake within the target tissue prior to light administration. Incubation can be accomplished using a relatively non-invasive procedure where the drug is administered intravenously into access graft sites that are isolated from circulation with vessel clamps, balloons or loops for appropriate time intervals.

Alternatively, local delivery catheters that deliver the drug to the site of interest could be used to deliver drugs to endovascular sites to be treated.

Another way to achieve local drug uptake is through a sleeve or cuff placed around the vessel within which the drug is incubated. The vessel sleeve can be used to keep the drug in contact with the vessel wall until a sufficient dosage has diffused into the target tissue for inhibition of stenosis or into the target lesion for suppression of stenosis.

Another method of local drug delivery is by applying a semisolid substance (e.g., a gel-like substance or paste) containing the drug to the outside of the vessel to keep the drug in contact with the vessel wall.

Additional local drug delivery techniques could utilize boundary layer infusion using an expanded polytetraflouroethylene (ePTFE) based local infusion device that delivers therapeutic agents directly through the wall of a synthetic graft. This method makes it possible to achieve high concentrations in the blood fluid boundary layer along the graft wall and downstream anastomotic sites.

Impregnation of vascular grafts such that the drug can diffuse into the target tissue is another method of local photosensitizer delivery.

Following drug delivery, the anastomotic area of the blood vessel is then exposed to a source of light having a wavelength suitable for photoactivating the photosensitive compound. Light can be applied before graft implantation at the intended anastomotic areas (i.e., where the anastomosis is going to be). Alternatively, the anastomotic areas of the blood vessels could be treated post graft implantation. Other areas where stenosis develops in AV access fistulas and grafts could be treated in the same way.

Light can be delivered using a variety of methods. Light can be delivered to the surgically exposed anastomotic area using an external light source. Alternatively, light can be delivered using an endolumenal light delivery catheter. When no shield is used, this light source is preferably limited to a wavelength of 610 nm or less to protect underlying tissue from inadvertent PDT treatment. Such a short wavelength approach is especially beneficial when using systemic drug delivery. If treatment is conducted using light of a short wavelength (wavelengths of 610 nm or less) excess blood surrounding the light delivery balloon is preferably removed to prevent attenuation of light by blood. In AV access grafts blood is flowing from a high-pressure arterial system into a low-pressure venous system, which could cause the vein to dilate around the balloon allowing blood to pass. This can be avoided by temporarily occluding blood flow proximal to the target anastomosis during the treatment. A double balloon approach with one balloon in the artery for blood occlusion and a light delivery balloon in the vein can also be used to occlude the artery. This approach of using short wavelength light and a proximal occlusion balloon is especially preferable for treatment of stenosis in an existing access graft. Light can also be delivered transcutaneously following local delivery of the photosensitizer to the anastomotic area.

When delivering light externally to the surgically exposed anastomosis or when using long wavelength light (wavelength of greater than 610 nm), a temporary shield can be placed underneath the exposed AV access graft to protect surrounding tissue from inadvertent PDT treatment. Such a shield is preferably used when light delivery is by means of an intralumenal device having emission at a deeply penetrating wavelength (wavelength greater than 610 nm) or when light delivery is by means of an external light delivery device having emission at any wavelength. Alternatively, a permanent, opaque cuff/sleeve can be placed around the area of lesion development at the time of graft implantation. The permanent cuff/sleeve allows for intralumenal treatment with shielding at a later time without exposing the AV access graft. The cuff or sleeve preferably has optical properties that prevent significant transmission at the treatment wavelength. The use of shielding is particularly beneficial when using long wavelength light, especially when systemic drug delivery is used.

In one embodiment of the invention, the vein is occluded on either side of the intended anastomosis site. A graft is connected at the venous anastomotic site, but not at the arterial anastomotic site. The graft is then used as a port to flush the vein, with the unattached arterial end providing a port for drug delivery. The drug is introduced through the graft and into the vein through the unattached arterial end. The drug is incubated in the vein for an appropriate time to allow the compound to diffuse into the wall of the vein. Following drug incubation, the drug is preferably flushed from the vein. If a PDT drug is used, light is delivered to the venous anastomosis and immediately adjacent region of the vein. Light can be delivered externally or by intravascular delivery. In the case of intravascular delivery, the light delivery device can be inserted into the vein at a site either proximal or distal to the anastomosis, or through the unattached arterial end of the graft. After light delivery, the artery is occluded to limit blood flow and the graft is attached to the arterial anastomosis. If the arterial anastomotic area is treated, the same approach is preferably used except in this case access to the artery is provided via an arterial incision prior to graft attachment.

One of the advantages of this method is that it limits the number of vascular access points necessary to perform the procedure, which is desirable because creation of access sites can cause injury that leads to the development of stenotic lesions. This method of using the graft attached to the vein also provides a very convenient means for accessing the treatment zone to decrease procedure time and minimize leakage of drug from the vessel.

The above-described method of drug delivery provides an effective method for local drug delivery in other types of grafts and can be employed with techniques for inhibiting stenosis using drug treatments that do not involve PDT. The classes of non-PDT drugs or drug combinations delivered using this method preferably have cytotoxic or cytostatic properties or properties that inhibit cell migration, which can reasonably be expected to inhibit the development of stenotic lesions.

Examples of such classes of drugs include, but are not limited to, sugars, peptides or proteins including hormones, glycoproteins, phosphoproteins, nucleic acids, polynucleotides, oligonucleotides, RNA, DNA, synthetic gene constructs, modified nucleotides, modified polynucleotides, modified oligonucleotides, anti-sense oligonucleotides, viral polynucleotides, plasmids (e.g., Bluescript, pUC, M13, etc.), lambda vectors, Yeast Artificial Chromosome vectors, lipids, lipoproteins, viruses and modified and attenuated viruses, drugs which have anticoagulative properties, anti-hypertensive agents, vasodilatory agents, anti-anginal agents, anti-diuretic agents, eicosanoids, prostaglandins, histamines, chelating agents, agents used for sclerotherapy including saline solutions or detergents, cytotoxic and chemotherapeutic agents including taxol and its naturally-occurring and synthetic derivatives, drugs aimed at inducing apoptosis, anti-angiogenic agents, cell cycle modifying agents, hydrophilic molecules, polar molecules, hydrophobic molecules, charged molecules (e.g., ions), amphipathic molecules, encapsulated molecules. In certain embodiments the drug includes, but is not limited to cytotoxic and chemotherapeutic agents including taxol and its naturally-occurring and synthetic derivatives; antineoplastics including 5-fluorouracil, bleomycin, and analogues thereof, prostaglandins and analogues thereof; chemotherapy agents including, but not limited to vincristine and platinum containing agents and analogues thereof, drugs aimed at inducing apoptosis including but not limited to ursodeoxycholate; anti-angiogenic agents including, but not limited to endostatin, angiostatin and inhibitors of the VEGF receptor mediated signaling pathway; cell cycle modifying agents including, but not limited to inhibitors of cyclin dependent kinases such as flavopiridol and agents which enhance expression or activity of tumor suppressor genes, or agents which modify signal transduction pathways including drugs which modify phosphorylation or phosphatase activity. In other embodiments the drug includes, but is not limited to, agents which inhibit cell migration including inhibitors of matrix metallo-proteases. In certain other embodiments, the drug includes, but is not limited to, peptides or proteins, hormones, analgesics, anti-migraine agents, anti-coagulant agents, anti-emetic agents, cardiovascular agents, anti-hypertensive agents, narcotic antagonists, chelating agents, anti-anginal agents, sedatives, diuretics or antidiuretic agents, bradykinins, eicosanoids, histamines and osmolality modifiers including mannitol. In certain other embodiments, the drug includes, but is not limited to, peptides, proteins or hormones including insulin, calcitonin, calcitonin gene regulating protein, somatropin, somatotropin, somatostatin, atrial natriuretic protein colony stimulating factor, betaseron, erythropoietin (EPO), luteinizing hormone release ID hormone (LHRH), tissue plasminogen activator (TPA), interferons including alpha-, beta- or gamma-interferon, insulin-like growth factor (somatomedins), growth hormone releasing hormone (GHRH), oxytocin, estradiol, growth hormones, leuprolide acetate, factor VIII, interleukins including interleukin-2, and analogues thereof; analgesics including fentanyl, sufentanil, hydrocodone, oxymorphone, methodone, butorphanol, buprenorphine, levorphanol, diclofenac, naproxen, morphine, hydromorphone, lidocaine, bupivacaine, paverin, and analogues thereof; anti-migraine agents including sumatriptan, ergot alkaloids, and analogues thereof; anti-coagulant agents including heparin, hirudin, and analogues thereof; anti-emetic agents including scopolamine, ondanesetron, domperidone, metoclopramide, and analogues thereof; cardiovascular agents, anti-hypertensive agents and vasodilators including diltiazem, nifedipine, verapamil, clonidine, isosorbide-5-mononitrate, organic nitrates, agents used in the treatment of heart disorders, and analogues thereof; sedatives including benzodiazepines, phenothiozines, and analogues thereof; narcotic antagonists including naltrexone, naloxone, and analogues thereof; chelating agents including desferoxamine, and analogues thereof; anti-diuretic agents including desmopressin, vasopressin, and analogues thereof; anti-anginal agents including nitroglycerine, and analogues thereof. In certain other embodiments, the drug includes, but is not limited to, anti-infectives including antibiotics and anti-viral agents; analgesics and analgesic combinations; anorexics; anti-helminthics; anti-arthritics including non steroidal anti-inflammatory agents (NSAIDS) and inhibitors of the cyclo-oxygenase enzyme family including but not limited to aspirin, piroxicam, ketorolac, rofecoxib, celecoxib and tiaprofenic acid; hypnotics; immunosuppressives; muscle relaxants; parasympatholytics; anti-asthmatic agents; anti-parkinsonism drugs; anti-pruritics; anti-psychotics; anti-convulsants; anti-depressants; anti-diabetic agents; anti-diarrheals; anti-histamines; anti-migraine preparations; anti-nauseants; anti-neoplastics; anti-pyretics; anti-spasmodics; anti-cholinergics; sympathomimetics; xanthine derivatives; central nervous system stimulants; cough and cold preparations, including anti-histamine decongestants; cardiovascular preparations including calcium channel blockers, beta-blockers including pindolol, anti-arrhythmics, anti-hypertensives, diuretics, and vasodilators including those acting on the general coronary, peripheral and cerebral vascular system; hormones including the estrogens, estradiol and progesterone and other steroids, including corticosteroids; psychostimulants; sedatives; tranquilizers, and analogs of any of the above. Other drugs which can be delivered using the described method to provide a therapeutic effect include those described in U.S. Pat. Nos. 5,997,501; 5,993,435; 5,916,910; 5,980,948; 5,980,932, the disclosures of which are incorporated herein by reference in their entirety.

EXAMPLE

The work described below was undertaken to evaluate the effects of application of an embodiment of the method of the present invention on the suppression of stenosis in a canine model of prosthetic AV access graft.

Preliminary studies using a new Chlorin-based photosensitive drug (MV6401, Miravant Medical Technologies) by both HPLC and fluorescence microscopy showed its incorporation into stenotic lesions and surrounding vessel wall. Initial studies using light-treatment without MV6401 confirmed no effect on the stenosis. Bilateral femoral PTFE AV access grafts were implanted in four female mongrel dogs. MV6401 (2 mg/kg, IV) was given one hour prior to the operation, and PDT was administered using an endolumenal non-thermal balloon catheter light source immediately after AV access graft placement. The contralateral side received a sham balloon treatment without light activation. The animals were sacrificed four weeks after the treatment, at which time the grafts were harvested, sectioned and examined by histology. Venous anastomotic sites were graded by an individual blinded to the treatment parameters and graded on a categorical scale (0–5) of lesion progression. Thickness of the stenotic lesion was determined using computer morphometry.

All AV access grafts were patent and fully functioning at four weeks. PDT-treated lesions showed significant reduction in the development of graft fibrosis (2.25±0.08 vs 1.13±0.15, P=0.02) that is a major component of stenotic lesions. As shown in FIGS. 2A and 2B, thickness of the stenotic lesions was significantly reduced 4 weeks after PDT treatment (1.51±0.11 mm vs 0.49±0.06 mm, P=0.006).

Thus, PDT treatment in accordance with the method described herein at the time of AV access graft placement significantly reduced the development of venous anastomotic stenosis and fibrosis at four weeks post-treatment. This result indicates that the method provides a safe and effective means for reducing stenosis at the anastomosis in AV access. This demonstration of a safe yet effective therapy is significant since the PDT dose used was sufficient to cause substantial acellularity in the vessel wall. In particular, the PDT dose was sufficient to substantially deplete the cell population in the vessel wall, yet there were no detrimental long term effects noted and substantial inhibition of stenosis was achieved with this approach.

Although the invention has been described with reference to specific embodiments, it will be understood by those skilled in the art that various changes may be made without departing from the spirit or scope of the invention. For instance, the numerous details set forth herein, for example, details relating to the study of the canine model described as an example herein, are provided to facilitate the understanding of the invention and are not provided to limit the scope of the invention. Accordingly, the disclosure of embodiments of the invention is intended to be illustrative of the scope of the invention and is not intended to be limiting. It is intended that the scope of the invention shall be limited only to the extent required by the appended claims.

We claim:

1. A method for inhibiting stenosis associated with an arteriovenous access graft connecting two blood vessels, wherein the two blood vessels each have an anastomotic area, the method comprising the steps of:
    (a) contacting at least one of the two blood vessels with a photosensitive compound;
    (b) implanting the graft; and
    (c) exposing target tissue comprising the anastomotic area of the contacted blood vessel to a source of light having a wavelength suitable for photoactivating the photosensitive compound for a period of time sufficient to provide a therapeutic effect.

2. The method of claim 1, wherein the therapeutic effect comprises producing at least partial acellularity within the target tissue.

3. The method of claim 1, wherein the target tissue is exposed to the source of light before graft implantation.

4. The method of claim 1, wherein the target tissue is exposed to the source of light after graft implantation.

5. The method of claim 1, wherein the step of contacting at least one of the two blood vessels with a photosensitive compound comprises the step of delivering photosensitive agents directly through a wall of the graft using a local infusion device.

6. The method of claim 1, wherein the step of contacting at least one of the two blood vessels with a photosensitive compound comprises the step of impregnating the anastomotic area using local photosensitizer delivery.

7. The method of claim 1, wherein the step of contacting at least one of the two blood vessels with a photosensitive compound comprises the step of endolumenally incubating the photosensitive compound for a sufficient time to allow the compound to diffuse into a wall of the contacted vessel.

8. The method of claim 7, wherein a portion of the contacted blood vessel is isolated from circulation and the photosensitive compound is administered into the isolated portion of the contacted blood vessel.

9. The method of claim 1, wherein the step of contacting at least one of the two blood vessels with a photosensitive compound comprises the step of the delivering the photosensitive compound to the contacted blood vessel by a local delivery catheter.

10. The method of claim 1, wherein the step of contacting at least one of the two blood vessels with a photosensitive compound comprises the step of placing a sleeve or cuff around the contacted blood vessel and incubating the photosensitive compound within the sleeve or cuff so that the photosensitive compound is kept in contact with a wall of the contacted blood vessel for a sufficient time to allow the compound to diffuse into the target tissue.

11. The method of claim 1, wherein the step of contacting at least one of the two blood vessels with a photosensitive compound comprises the step of applying a semisolid substance comprising the photosensitive compound to a wall of the contacted blood vessel.

12. The method of claim 1, wherein the target tissue is exposed to a source of light using a light delivery balloon catheter.

13. The method of claim 12, wherein the two blood vessels are a vein and an artery, and wherein the step of exposing target tissue to a source of light further comprises the step of temporarily occluding the artery to prohibit or limit the flow of blood during light exposure.

14. The method of claim 13, wherein a balloon catheter is inserted into the artery for temporarily occluding the artery.

15. The method of claim 1, wherein the step of exposing target tissue to a source of light further comprises the step of placing a shield underneath at least the anastomotic area of the contacted blood vessel to protect surrounding tissue.

16. The method of claim 1, further comprising the step of implanting a cuff or sleeve around at least the anastomotic area of the contacted blood vessel at the time of implantation of the arteriovenous access graft to allow intralumenal treatment with shielding alter implantation of the arteriovenous access graft.

17. A method for inhibiting stenosis associated with an arteriovenous access graft connecting an artery and a vein, wherein the method is performed at the time of implantation of a graft material which will connect the artery and the vein, the method comprising the steps of:

(a) isolating from circulation a portion of the vein to which the graft material will be attached;

(b) introducing a dosage of photosensitive compound into the isolated portion of the vein;

(c) endolumenally incubating the photosensitive compound for a sufficient period of time to allow the compound to diffuse into tissue of the vein;

(d) attaching the graft material to the isolated portion of the vein, thereby forming an anastomosis having an associated anastomotic area;

(e) placing a shield underneath the vein to protect surrounding tissue; and (f) inserting a light-diffusing balloon catheter into the vein and exposing target tissue comprising the anastomotic area to light having a wavelength suitable for photoactivating the photosensitive compound for a period of time sufficient to provide a therapeutic effect.

18. A method for inhibiting stenosis associated with an arteriovenous access graft connecting an artery and a vein, wherein the method is performed at the time of implantation of a graft material which will connect the artery and the vein, the method comprising the steps of:

(a) contacting the vein with a photosensitive compound;

(b) allowing sufficient time to permit uptake of the photosensitive compound into the vein;

(c) attaching the graft material to the vein, thereby forming an anastomosis having an associated anastomotic area; and (d) exposing the anastomotic area to a source of light having a wavelength suitable for photoactivating the photosensitive compound for a period of time sufficient to provide a therapeutic effect.

* * * * *